United States Patent [19]

Yaginuma et al.

[11] Patent Number: 4,934,813
[45] Date of Patent: Jun. 19, 1990

[54] APPARATUS FOR INSPECTING AN INNER SURFACE OF A PIPE INCLUDING MEANS FOR PREVENTING HALATION

[75] Inventors: Yoshitaka Yaginuma; Isamu Hayashi, both of Naka, Japan

[73] Assignee: Mitsubishi Nuclear Fuel Co., Tokyo, Japan

[21] Appl. No.: 369,772

[22] Filed: Jun. 22, 1989

[30] Foreign Application Priority Data

Jun. 24, 1988 [JP] Japan .................................. 63-156518

[51] Int. Cl.$^5$ ............................................. G02B 23/26
[52] U.S. Cl. .................................................... 356/241
[58] Field of Search .......................................... 356/241

[56] References Cited

U.S. PATENT DOCUMENTS 3,413,067 11/1968 Froio .................................. 356/241
4,712,916 12/1987 Gunn .................................. 356/241

FOREIGN PATENT DOCUMENTS 61-80718 1/1961 Japan .
62-108219 5/1987 Japan .

OTHER PUBLICATIONS

Heinz, "Method of Checking Wall Imperfections", Western Electric Technical Digest No. 19, Jul. 1970, pp. 31-32.

Primary Examiner—Vincent P. McGraw
Attorney, Agent, or Firm—Cushman, Darby & Cushman

[57] ABSTRACT

In a pipe inner-surface inspecting apparatus, a body is inserted into an interior of the pipe and has an illuminator mounted at a forward end of the body for emitting light forwardly from the forward end of the body. A reflecting mirror in the form of a conical surface is so arranged as to face toward the forward end of the body with a space left between the reflecting mirror and the forward end of the body. The reflecting mirror diverges away from the forward end of the body, and reflects the light from the illuminator to illuminate the inner surface of the pipe thereby forming an image thereof. A concentrating unit is arranged at the forward end of the body for concentrating the image of the inner surface of the pipe, which is reflected by the reflecting mirror, to transmit the image to a rearward end of the body. A transparent glass is interposed between the reflecting mirror and the forward end of the body. The transparent glass has a surface in close contact with the reflecting mirror, which has a central region formed with a recess.

5 Claims, 3 Drawing Sheets

APPARATUS FOR INSPECTING AN INNER SURFACE OF A PIPE INCLUDING MEANS FOR PREVENTING HALATION

BACKGROUND OF THE INVENTION

The present invention relates to a pipe inner-surface inspecting apparatus for use in inspection for damage or the like on the inner surface of an elongated small-diameter pipe such as, for example, a covering pipe for a nuclear fuel bar, or the like.

A covering pipe for a nuclear fuel bar is formed by an elongated small-diameter pipe having an inner diameter on the order of 9 mm. The inventors of this application have already proposed an apparatus for inspecting an inner surface of an elongated small-diameter pipe visually, in Japanese Utility Model Application No. SHO 61-80718. As shown in FIGS. 2 through 5 of the accompanying drawings of this invention, the apparatus comprises a bore scope 2 serving as a body inserted into the interior of the pipe 1 that is the subject of inspection, and a transparent glass means 3 that supports a reflecting mirror 4 which is arranged at a location spaced a predetermined distance from the forward end of the bore scope 2. The apparatus will be described below in brief.

As shown in FIGS. 2 and 3, the bore scope 2 has an image transmitting path 6 at the center of a stainless steel tube 5 whose outer diameter is slightly less than the inner diameter of the pipe 1. The image transmitting path 6 is formed by an optical fiber bundle or a combination of a plurality of lenses. The image transmitting path 6 has a forward end at which a concentrating lens system 7 is arranged. The concentrating lens system 7 has a visual field angle within the range $\theta$. Arranged about the outer periphery of the image transmitting path 6 is a cylindrical light guide 8 which is composed of an optical fiber bundle. The light guide 8 has a rearward end which is optically connected to a light source (not shown). A forward end of the light guide 8 is formed into an illuminating section 8a for emitting light transmitted from the light source, axially into the pipe 1.

The transparent glass means 3 serving as transparent glass means is cylindrical in shape having a diameter substantially equal to the outer diameter of the bore scope 2. The transparent glass means 3 has one end end thereof which is mounted to the forward end of the bore scope 2 in contact therewith. The other end of the transparent glass means 3 is formed with a conical recess 3a. The conical recess 3a is formed to have a predetermined angle determined on the basis of the optical system and the illuminating system of the bore scope 2. The conical recess 3a is spaced a distance from the forward end of the bore scope 2. A portion of the conical surface of the recess 3a, except for a central or bottom portion and an edge portion thereof, is coated with a silver coating or the like to form or finish a reflecting mirror 4. The reflecting mirror 4 is so arranged as to diverge away from the forward end of the bore scope 2.

A guide member 9 made of resinous material or the like is fixedly mounted to the conical surface 3a of the transparent glass means 3 which is formed into the reflecting mirror 4. Specifically, the guide member 9 has an outer peripheral surface 9a which is in contact with the inner peripheral surface of the pipe 1, and a conical section 9b complementary to the conical surface 3a of the transparent glass means 3 which is formed into the reflecting mirror 4. The conical section 9b is in close contact with the conical surface 3a of the transparent glass means 3.

Further, as shown in FIG. 5, the pipe 1 is mounted on the upper surface of a fixing table 10. The fixing table 10 has one end thereof at which a base 12 is arranged. Arranged within the base 12 is an inserting device 11 for inserting the bore scope 2 and the transparent glass means 3 into the pipe 1. The inserting device 11 is composed of a plurality of support rollers 13 for supporting the bore scope 2 and the transparent glass means 3, and a drive mechanism 14 for inserting the bore scope 2 and the transparent glass means 3 into he pipe 1. Arranged at an end of the base 12 on the side to the other end of the fixing table 10 is an inserting and positioning section 15 for inserting the bore scope 2 into the pipe 1. The bore scope 2 has a rearward end to which an industrial television camera 16 is fixedly mounted. The television camera 16 has an image capture lens system which is connected to the rearward end of the image transmitting path 6 in the bore scope 2. The image on the television camera 16 is sent to an automatic inner-surface image processor 17 which comprises a video tape recorder 18 for recording the image, a monitor television 19 for displaying the image, and an operating panel 20 for operating these instruments 18 and 19. Predetermined processing of the image is carried out by the automatic inner-surface image processor 17.

The conventional pipe inner-surface inspecting apparatus is constructed as described above. With such a construction, when the driving mechanism 14 of the inserting device 11 is operated to insert the transparent glass means 3 and the bore scope 2 into the pipe 1 at the head of the guide member 9, the light emitted from the illuminating section 8a of the light guide 8 in the bore scope 2 passes through the transparent glass means 3 and is reflected by the reflecting mirror 4, thereby brightly illuminating the entire periphery of the inner surface of the pipe 1. An image of the entire periphery of the inner surface of the pipe 1 is reflected by the reflecting mirror 4 and reaches the concentrating lens system 7 at the forward end of the bore scope 2. The image reaching the concentrating lens system 7 is transmitted to the television camera 16 through the image transmitting path 6.

In the case of the conventional apparatus, as shown in FIG. 2, a range of the inner peripheral surface of the pipe 1, reaching the concentrating lens system 7, that is, a viewing range thereof is the section indicated by the character A which is composed of a portion $A_1$ and a portion $A_2$. The portion $A_1$ is the portion reflected by the reflecting mirror 4 and is reflected in approximately a straight line. The portion $A_2$ is the portion of the inner peripheral surface of the pipe 1 which is directly reflected by the inner peripheral surface of the pipe 1 into the concentrating lens system 7. In an image in which the range A is transmitted to the television camera 16, as shown in FIG. 4, the entire image $A_1$ reflected by the reflecting mirror 4 is cast on the central region of the television camera 16, and the entire peripheral image $A_2$ which is directly reflected into the concentrating lens system 7 is cast on the outside of the image $A_1$.

Under these circumstances, when the driving mechanism 14 is operated to cause the transparent glass means 3 and the bore scope 2 to advance into the pipe 1, the entire peripheral image of the inner surface of the pipe 1 is continuously taken out through the entire length of the pipe 1 and is transmitted to the television camera 16.

The image of the inner surface of the pipe 1, which is transmitted to the television camera 16, is displayed on the monitor television 19 in real time. A defective portion or portions of the inner surface of the pipe 1 are found by the image processing. The image processing is recorded by the video tape recorder 18. Thus, it is possible to judge or determine as to whether or not a damage or damages such as mars or cracks occur in the inner surface of the pipe 1.

In the conventional pipe inner-surface inspecting apparatus, however, it is difficult to accurately finish the central portion of the conical recess 3a of the transparent glass means 3 with which the reflecting mirror 4 is in close contact. Further, there is also a problem that halation occurs due to the light reflected at the central portion of the conical recess 3a. Moreover, since the pipe inner surface is generally mirror-finished, defective portions of the inner surface of the pipe 1 are more easily detected if the pipe inner surface is illuminated with a diffused light source.

SUMMARY OF THE INVENTION

It is therefore an object of the invention to provide a pipe inner-surface inspecting apparatus in which a transparent glass means allows easy finish-processing of the pipe inner-surface and in which halation is prevented, so that it is possible to inspect for a defect or defects on an inner surface of a pipe in a clearer manner.

According to the invention, there is provided an apparatus for inspecting the inner surface of a pipe comprising:

a body inserted into the interior of the pipe and having an illuminating means mounted at the forward end of the body for emitting light forwardly from the forward end of the body in a direction parallel to the longitudinal axis of the pipe;

a reflecting mirror means in the form of a conical surface arranged so as to face toward the forward end of the body with a space left between the reflecting mirror means and the forward end of the body, the reflecting mirror means diverging away from the forward end of the body, the reflecting mirror means reflecting the light from the illuminating means to illuminate the inner surface of the pipe thereby forming an image of the inner surface of the pipe;

the body including means arranged at the forward end of the body for concentrating the image of the inner surface of the pipe, which is reflected by the reflecting mirror means, to transmit the image to a rearward end of the body; and a transparent glass means interposed between the reflecting mirror means and the forward end of the body, the transparent glass means having a surface in close contact with the reflecting mirror means, the surface of the transparent glass means having a central region which is formed with a recess.

With the apparatus constructed as above, the recess formed at the central region of the surface of the transparent glass means can ensure to prevent occurrence of halation caused by the light reflected at the central region of the surface of the transparent glass means with which the reflecting mirror means is in close contact. In addition, the reflected light from the recess can brightly illuminate the inner surface of the pipe so that the defect or defects on the inner surface of the pipe can be viewed more easily. Thus, it is possible to inspect the inner surface of the pipe in a smoother manner. Further, the invention has an advantage in that it is easy to manufacture the transparent glass means.

Preferably, the recess in the surface of the transparent glass means is filled with an opaque material. The opaque material can further ensure to eliminate the halation.

DETAILED DESCRIPTION OF THE PREFERRED EMBODIMENT

Figure 1:
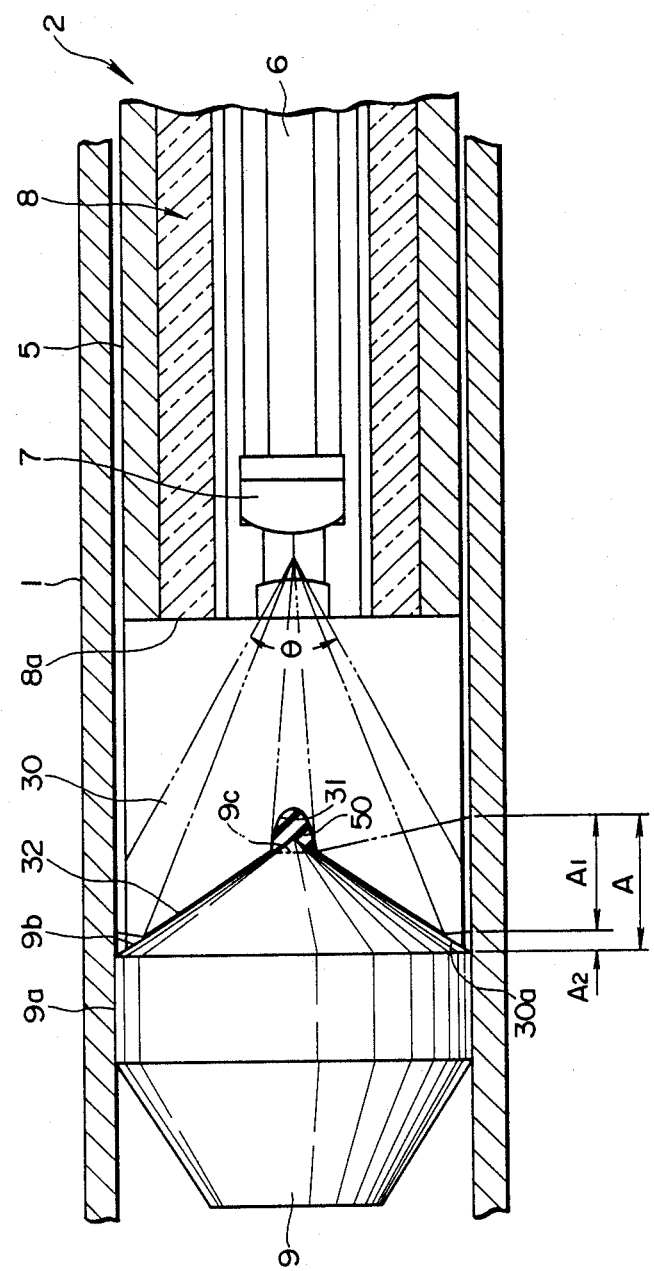
FIG. 1 is a cross-sectional view of a pipe inner-surface inspecting apparatus according to an embodiment of the invention.
Figure 2:
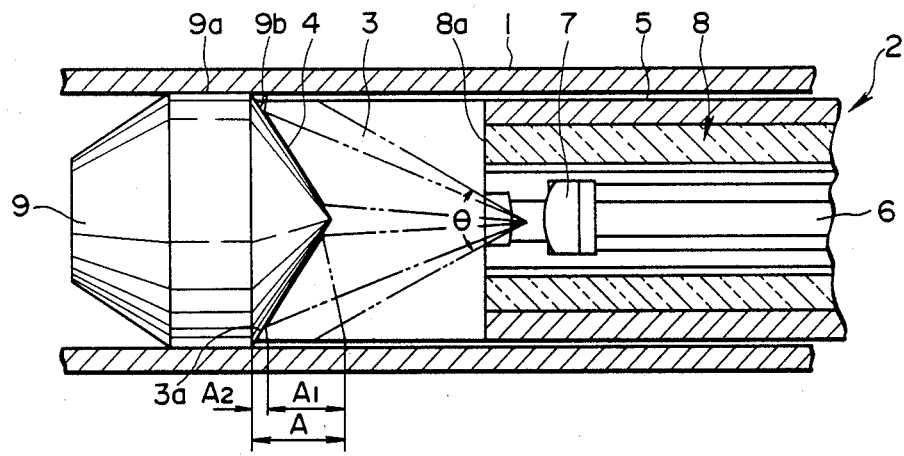
FIG. 2 is a view similar to FIG. 1, but showing a conventional apparatus.
Figure 3:
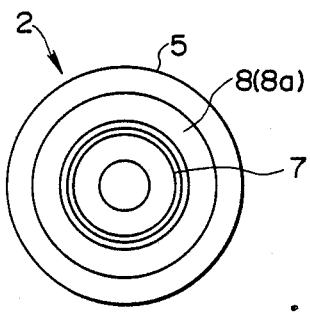
FIG. 3 is a front elevational view or the bore scope illustrated in FIG. 2.
Figure 4:
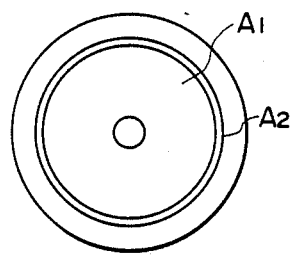
FIG. 4 is a view for explanation of an entire peripheral image of an inner surface of a pipe, the image being obtained by the use of the apparatus illustrated in FIG. 2.
Figure 5:
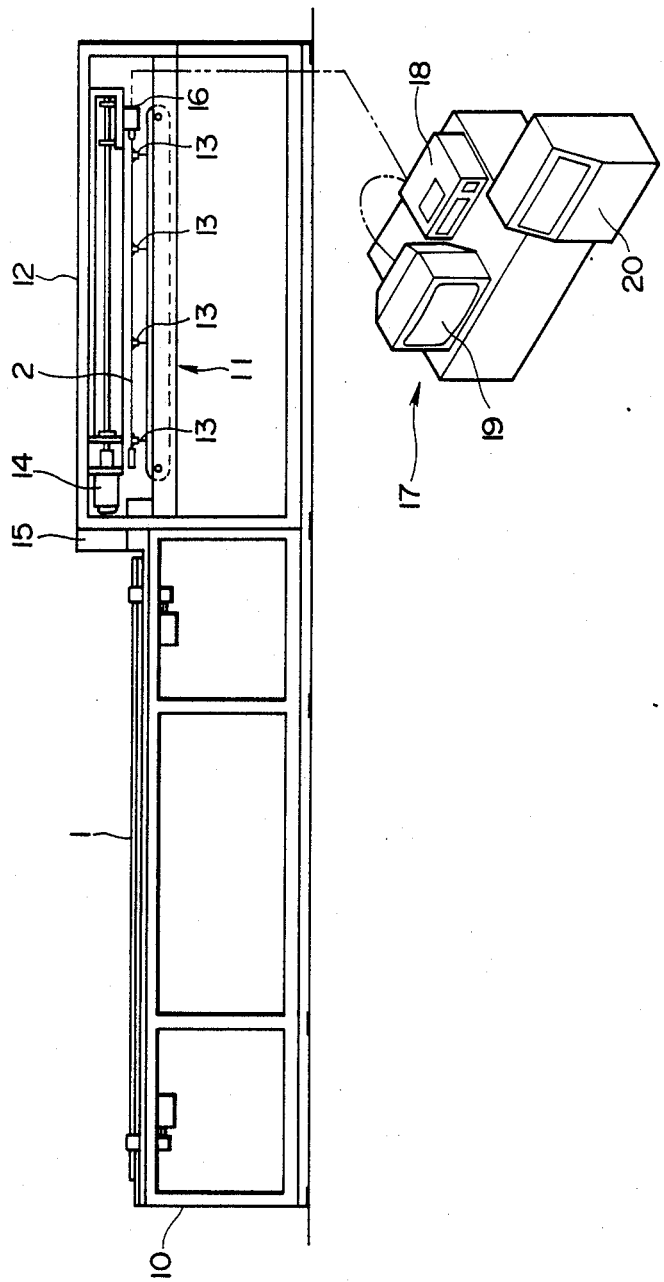
FIG. 5 is a side elevation view of an entire system of the apparatus illustrated in FIG. 2.

Referring to FIG. 1, there is shown a pipe inner-surface inspecting apparatus according to an embodiment of the invention. The apparatus is different from the conventional apparatus illustrated in FIGS. 2 through 5 only in that a new transparent glass means 30 serving as transparent glass means is substituted for the transparent glass means 3. Other features and the arrangement of the apparatus illustrated in FIG. 1 are the same as those shown in FIGS. 2 through 5. Component parts like or similar to those of the apparatus illustrated in FIGS. 2 through 5 are designated by the same or like reference numerals, and the description of these same or like component parts will therefore be omitted to avoid duplication.

The transparent glass means 30 is cylindrical in shape, substantially the same in diameter as the bore scope 2. The transparent glass means 30 has one end thereof which is mounted to the forward end of the bore scope 2 in close contact therewith. The other end of the transparent glass means 30 is formed into a conical recessed surface 30a. The recessed surface 30a has a central region which is formed with a recess 31 having a curved surface. A portion of the recessed surface 30a, except for an edge portion thereof and a portion of the recess 31, is coated with a silver reflected layer or the like to form and finish a reflecting mirror 32. In this connection, it is preferable that the curved surface of the recess 31 is slightly or adequately roughened.

The pipe inner-surface inspecting apparatus according to the invention is constructed as above. When the apparatus is used to inspect the inner surface of the pipe 1, the transparent glass means 30 and the bore scope 2 are inserted into the pipe 1 at the head of the guide member 9 in a state in which the light from the light source is emitted from the illuminating section 8a through the light guide 8, in a manner like the conventional apparatus. The light emitted from the illuminating section 8a of the light guide 8 is transmitted through the transparent glass means 30 and is reflected by the reflecting mirror 32 to brightly illuminate the entire inner surface of the pipe 1. The entire peripheral image of the inner surface of the pipe 1 is reflected by the reflecting mirror 32 and reaches the concentrating lens system 7 at the forward end of the bore scope 2. The image is transmitted to the television camera through the concentrating lens system 7 and the image transmitting path 6.

In the case of the apparatus according to the invention, the recess 31 having a preferably roughened curved surface is formed at the center of the recessed surface 30a of the transparent glass means 30. Accordingly, the light is diffusedly reflected by the recess 31 so that halation does not occur. Further, the light reflected at the recess 31 makes it possible to illuminate the interior of the pipe 1 so that a defect or defects on the inner surface of the pipe 1 can be viewed more easily. Thus, it is possible to view the entire peripheral image of the inner surface of the pipe 1 in a more definite manner.

In connection with the embodiment described above, a portion of the conical section 9b of the guide member 9, which faces toward the recess 31 of the transparent glass means 30, has a conically pointed tip. As indicated by the double dotted line in FIG. 1, however, the portion 9c of the conical section 9b may be planar surface in a direction perpendicular to the axis of the pipe 1. Further, the recess 31 may be filled with an opaque material, for example, a silicone rubber of a white color which may be used as adhesive. In this case, there are obtained advantages similar to those of the embodiment described above.

What is claimed is:

1. An apparatus for inspecting an inner surface of a pipe that is a subject of inspection, said apparatus comprising:
    a body inserted into an interior of the pipe and having an illuminating means mounted at the forward end of said body for emitting light forwardly from the forward end of said body in a direction parallel to the longitudinal axis of the pipe;
    a reflecting mirror means in the form of a conical surface arranged so as to face toward the forward end of said body with a space left between said reflecting mirror means and the forward end of said body, said reflecting mirror means reflecting the light from said illuminating means to illuminate the inner surface of the pipe thereby forming an image of the inner surface of the pipe;
    said body including means arranged at the forward end of said body for concentrating the image of the inner surface of the pipe, which is reflected by said reflecting mirror means, to transmit the image to a rearward end of said body;
    a transparent glass means interposed between said reflecting mirror means and the forward end of said body, said transparent glass means having a surface in close contact with said reflecting mirror means, said surface of said transparent glass means having a central region which is formed with a recess; and
    an opaque material filled in said recess, said opaque material preventing halation at the central region of the surface of the transparent glass means.

2. An apparatus according to claim 1, wherein said recess has a curved surface.

3. An apparatus according to claim 2, wherein said curved surface of said recess is roughened.

4. An apparatus according to claim 1, further comprising a guide member having an outer peripheral surface in contact with the inner surface of the pipe and a conical section complementary to said reflecting mirror means, said guide member having a portion thereof facing toward said recess, said portion being planer surface in a direction perpendicular to an axis of the pipe.

5. An apparatus according to claim 1, wherein said body is a bore scope.

* * * * *